United States Patent [19]

Nuss, Jr. et al.

[11] 4,230,727
[45] Oct. 28, 1980

[54] COMPOSITIONS AND METHOD OF TREATMENT

[75] Inventors: George W. Nuss, Jr., Lansdale; Norman J. Santora, Roslyn; George H. Douglas, Malvern, all of Pa.

[73] Assignee: William H. Rorer, Inc., Fort Washington, Pa.

[21] Appl. No.: 26,334

[22] Filed: Apr. 2, 1979

Related U.S. Application Data

[63] Continuation-in-part of Ser. No. 839,960, Oct. 6, 1977.

[51] Int. Cl.² .................... A61K 31/19; A61K 31/135
[52] U.S. Cl. ...................................... 424/330; 424/317
[58] Field of Search ................................ 424/304, 330

[56] References Cited

U.S. PATENT DOCUMENTS

| | | | |
|---|---|---|---|
| 3,833,606 | 9/1974 | Mohan | 260/566 F |
| 3,862,833 | 1/1975 | Johnson et al. | 260/566 F |
| 4,047,803 | 9/1977 | Yaguchi et al. | 260/566 F |
| 4,122,026 | 10/1978 | Osman | 260/566 F |

OTHER PUBLICATIONS

Kadoba et al., J. Heter. Chem., vol. 4, pp. 301-304, (1967).
Goetz, J. Heter. Chem., vol. 5, pp. 501-507, (1968).
Bellobono et al., Tetrahedron, vol. 25, pp. 57-71, (1969).
Ogata et al., J. Chem. Soc., Perkins Trans., vol. 2, pp. 792-797, (1972).
Favini et al., Gazz. Chem. Ibol., vol. 96, pp. 1423-1431, (1966).

*Primary Examiner*—Stanley J. Friedman
*Attorney, Agent, or Firm*—Miller & Prestia

[57] ABSTRACT

Compositions for inhibiting cellular proliferation in mammals containing as the active ingredient N-benzylideneaniline and its derivatives, and the method therefor.

27 Claims, No Drawings

COMPOSITIONS AND METHOD OF TREATMENT

This application is a continuation-in-part of Application Ser. No. 839,960, filed Oct. 6, 1977.

BACKGROUND OF THE INVENTION

Hyperproliferation of epidermal cells in mammals can be induced virally as well as by body dysfunctions. Herpes simplex and herpes zoster infections are examples of the virally-induced cell growth initiators. Cold sores are further examples of virus-induced cellular proliferation conditions. Psoriasis is a skin disease characterized by an apparent disruption in a number of regulatory functions. Both the length of cell cycle and cell turnover time are considerably shortened in the epidermis of such infected skins. The rapidly growing epidermal cells also fail to differentiate normally. Anti-psoriasis drugs such as methotrexate, anthralin, cytosine arabinoside and daunorubicine have been found to inhibit cell proliferation by inhibiting the thymidine or deoxyuridine incorporated into DNA so as to prevent protein growth.

It is known from *Experientia* 29, 1442–43, 1559–1561 (1973) and 30, 1272 (1974) that 2-amino-4,6-dichloropyrimidine is effective to inhibit the growth of polio virus in vitro by interfering with the intercellular assembly of the viral particle. It acts as the stage of the capsid precursors, impairing structural protein VPO formation.

The compounds of the present invention are known to have anti-inflammatory activity and to be useful in the protection of the human skin against the harmful effects of radiation.

It has been surprisingly found in accordance with the present invention that certain anti-inflammatory compounds possess the additional ability to act as metabolic inhibitors in the growth of epidermal cells in those conditions caused by viral infections as well as of non-specific origin. The combination of useful properties permits the compounds of the present invention to be applied not only to obtain relief from existing inflammatory conditions of the skin but to further act as an inhibitor of skin rashes caused by cellular proliferation due to the underlying condition.

BRIEF DESCRIPTION OF THE INVENTION

The present invention pertains to a novel method and preparations for inhibiting cellular proliferation in mammals by impairing structural protein formation through the use of a compound of the formula:

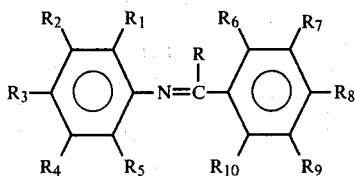

where:
R. is hydrogen or alkyl;
$R_1, R_2, R_3, R_4, R_5, R_6, R_7, R_8, R_9$, and $R_{10}$ may be the same or different and are
hydrogen,
alkyl,
cyano,
nitro,
amino,
haloloweralkoxy,
haloloweralkyl,
halo,
loweralkoxy,
acyl,
acyloxy,
thio,
acylthio,
loweralkylthio,
loweralkylsulfinyl,
loweralkylsulfonyl;
hydroxy,
carboxy, and
carbalkoxy;

$R_3$ and $R_8$ may also be cycloalkyl, cycloalkenyl, aryl, and heteroloweralkylidenyl.

DETAILED DESCRIPTION OF THE INVENTION

The preparations provided in accordance with the present invention contain as the essential active ingredient a compound of the formula:

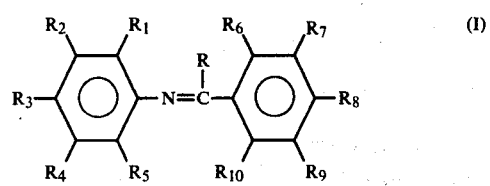

where:
R is hydrogen or alkyl;
$R_1, R_2, R_3, R_4, R_5, R_6, R_7, R_8, R_9$ and $R_{10}$ may be the same or different and are
hydrogen,
alkyl,
cyano,
nitro,
amino,
haloloweralkoxy,
haloloweralkyl,
halo,
loweralkoxy,
acyl,
acyloxy,
thio,
acylthio,
loweralkylthio,
loweralkylsulfinyl,
loweralkylsulfonyl;
hydroxy,
carboxy, and
carbalkoxy;

$R_3$ and $R_8$ may also be cycloalkyl, cycloalkenyl, aryl, and heteroloweralkylidenyl.

The more preferred compounds for a method of inhibiting epidermal cells from proliferating embrace those compounds of the Formula II:

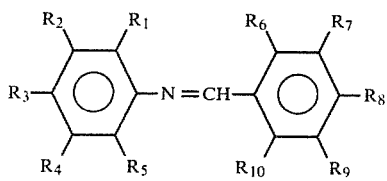

where:
R$_1$, R$_2$, R$_4$, R$_5$, R$_6$, R$_7$, R$_9$ and R$_{10}$ are
   hydrogen,
   alkyl,
   alkoxy,
   halo,
   haloloweralkyl,
   hydroxy,
   carboxy,
   carbalkoxy, and
   alkylsulfonyl.
R$_3$ and R$_8$ are
   hydrogen,
   alkyl,
   alkoxy,
   carboxy,
   carbalkoxy,
   halo,
   cyano,
   alkylsulfonyl,
   alkylsulfinyl,
   haloloweralkyl,
   phenyl, and
   cyclohexyl.

In the descriptive portions of this invention, the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to about 7 carbon atoms which may be straight chained or branched;

"cyaloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid by the removal of its hydroxyl group such as formyl, acetyl, propionyl, 3-carboxy-2-propenoyl, camphoryl, benzoyl, toluoyl or heteroyl such as pyridinoyl, piperidonyl, thenoyl, etc.

The compounds of this invention may be prepared by the following general procedures.

Condensation of an aniline derivative with benzaldehyde derivatives or phenyl ketones along the procedures as described by Gillman and Blatt, *Organic Synthesis*, Coll. Vol. I, 2nd Ed., N.Y., John Wiley and Sons, pages 80–81 will result in the desired product.

The following reaction equation illustrates this synthesis:

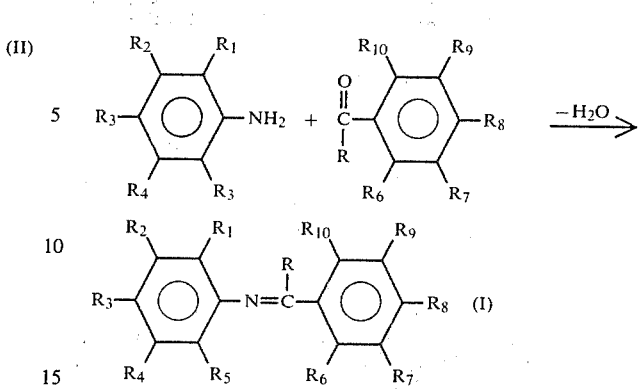

where R, R$_1$, R$_2$, R$_3$, R$_4$, R$_5$, R$_6$, R$_7$, R$_8$, R$_9$ and R$_{10}$ are as described above.

An alternate method for the production of certain compounds of Formula I involves the distillation of a product from a heated mixture of an aryl aldehyde or ketone and an aniline derivative at an elevated temperature and under a reduced pressure.

A still further method of preparing certain compounds of Formula I would be by condensation of a hindered aryl aldehyde or ketone and an aniline derivative by the azeotropic removal of water.

Appropriately desired end products having various substituents can be prepared at various stages of synthesis using suitable reactions in order to convert one group to another. Thus, for example, using conventional methods, a halogen group can be converted under Rosenmund Von Braun conditions to the nitrile compound. A nitro can be reduced to an amino which can be alkylated to the dialkylamino substituent. An hydroxy compound can be prepared by demethylation of a methoxy substituent. A Sandmeyer type reaction can be carried out on an amino compound to introduce a chloro, bromo, xanthate, hydroxyl or alkoxy group. The xanthate can then lead to the mercapto by hydrolysis, this in turn can be alkylated to an alkylthio group which can be oxidized to alkylsulfinyl and alkylsulfonyl groups. A thiocyanato group may be removed by catalytic hydrogenation.

Among the suitable compounds which may be utilized in connection with the cell growth inhibiting compositions of the present invention include:
N-benzylideneaniline
N-(hydroxybenzylidene)aniline
N-(carboxybenzylidene)aniline
N-(carbomethoxybenzylidene)toluidine
N-carboethoxybenzylidene-m-toluidine
N-benzylidene-p-toluidine
N-(o-hydroxybenzylidene)-m-toluidine
N-(o-hydroxybenzylidene)-p-toluidine
N-(o-hydroxybenzylidene)-m-α,α,α-trifluorotoluidine
N-(o-hydroxybenzylidene)-o-α,α,α-trifluorotoluidine
N-benzylidene-o-ethylaniline
N-benzylidene-o-hydroxyaniline
N-benzylidene-m-hydroxyaniline
N-benzylidene-p-hydroxyaniline
N-(o-hydroxybenzylidene)-o-hydroxyaniline
N-(m-hydroxybenzylidene)-o-hydroxyaniline
N-(p-hydroxybenzylidene)-o-hydroxyaniline
N-(o-hydroxybenzylidene)-m-hydroxyaniline
N-(m-hydroxybenzylidene)-m-hydroxyaniline
N-(p-hydroxybenzylidene)-m-hydroxyaniline
N-(o-hydroxybenzylidene)-p-hydroxyaniline N-(m-hydroxybenzylidene)-p-hydroxyaniline
N-(p-hydroxybenzylidene)-p-hydroxyaniline
N-(2,3-dihydroxybenzylidene)-o-hydroxyaniline
N-(2,4-dihydroxybenzylidene)-o-hydroxyaniline
N-(2,5-dihydroxybenzylidene)-o-hydroxyaniline
N-(2,6-dihydroxybenzylidene)-o-hydroxyaniline
N-(3,4-dihydroxybenzylidene)-o-hydroxyaniline
N-(3,5-dihydroxybenzylidene)-o-hydroxyaniline
N-(2,3,4-trihydroxybenzylidene)-o-hydroxyaniline
N-(2,4,6-trihydroxybenzylidene)-m-hydroxyaniline
N-(3,4,5-trihydroxybenzylidene)-m-hydroxyaniline
N-(2,3-dihydroxybenzylidene)-p-hydroxyaniline
N-(2,4-dihydroxybenzylidene)-p-hydroxyaniline
N-(2,5-dihydroxybenzylidene)-p-hydroxyaniline
N-(2,6-dihydroxybenzylidene)-p-hydroxyaniline
N-(3,4-dihydroxybenzylidene)-p-hydroxyaniline
N-(3,5-dihydroxybenzylidene)-p-hydroxyaniline
N-(2,3,4-trihydroxybenzylidene)-p-hydroxyaniline
N-(2,4,6-trihydroxybenzylidene)-p-hydroxyaniline
N-(p-morpholinobenzylidene)aniline
N-(p-phenylbenzylidene)aniline
o-chlorobenzylideneaniline
m-chlorobenzylideneaniline
p-chlorobenzylideneaniline
N-benzylidene-o-chloroaniline
N-benzylidene-m-chloroaniline
N-benzylidene-p-chloroaniline
N-benzylidene-2,3-dichloroaniline
N-benzylidene-2,4-dichloroaniline
N-benzylidene-2,5-dichloroaniline
N-benzylidene-2,6-dichloroaniline
N-benzylidene-3,4-dichloroaniline
N-benzylidene-3,5-dichloroaniline
N-benzylidene-2,3,4-trichloroaniline
N-benzylidene-2,4,6-trichloroaniline
N-(o-chlorobenzylidene)-o-chloroaniline
N-(m-chlorobenzylidene)-o-chloroaniline
N-(p-chlorobenzylidene)-4-toluidine
N-(p-chlorobenzylidene)-o-chloroaniline
N-(o-chlorobenzylidene)-m-chloroaniline
N-(m-chlorobenzylidene)-m-chloroaniline
N-(p-chlorobenzylidene)-m-chloroaniline
N-(o-chlorobenzylidene)-p-chloroaniline
N-(m-chlorobenzylidene)-p-chloroaniline
N-(p-chlorobenzylidene)-p-chloroaniline
N-(o-chlorobenzylidene)-o-fluoroaniline
N-(m-chlorobenzylidene)-o-fluoroaniline
N-(p-chlorobenzylidene)-o-fluoroaniline
N-(o-chlorobenzylidene)-m-fluoroaniline
N-(m-chlorobenzylidene)-m-fluoroaniline
N-(p-chlorobenzylidene)-m-fluoroaniline
N-(o-chlorobenzylidene)-p-fluoroaniline
N-(m-chlorobenzylidene)-p-fluoroaniline
N-(p-chlorobenzylidene)-p-fluoroaniline
N-(2,3-dichlorobenzylidene)-o-chloroaniline
N-(2,4-dichlorobenzylidene)-o-chloroaniline
N-(2,5-dichlorobenzylidene)-o-chloroaniline
N-(2,6-dichlorobenzylidene)-o-chloroaniline
N-(3,4-dichlorobenzylidene)-o-chloroaniline
N-(3,5-dichlorobenzylidene)-o-chloroaniline
N-(2,3,4-trichlorobenzylidene)-o-chloroaniline
N-(2,4,6-trichlorobenzylidene)-o-chloroaniline
N-(2,3-dichlorobenzylidene)-m-chloroaniline
N-(2,4-dichlorobenzylidene)-m-chloroaniline
N-(2,5-dichlorobenzylidene)-m-chloroaniline
N-(2,6-dichlorobenzylidene)-m-chloroaniline
N-(3,4-dichlorobenzylidene)-m-chloroaniline
N-(3,5-dichlorobenzylidene)-m-chloroaniline
N-(2,3,4-trichlorobenzylidene)-m-chloroaniline
N-(2,4,6-trichlorobenzylidene)-m-chloroaniline
N-(2,3-dichlorobenzylidene)-p-chloroaniline
N-(2,4-dichlorobenzylidene)-p-chloroaniline
N-(2,5-dichlorobenzylidene)-p-chloroaniline
N-(2,6-dichlorobenzylidene)-p-chloroaniline
N-(3,4-dichlorobenzylidene)-p-chloroaniline
N-(3,5-dichlorobenzylidene)-p-chloroaniline
N-(2,3,4-trichlorobenzylidene)-p-chloroaniline
N-(2,4,6-trichlorobenzylidene)-p-chloroaniline
o-fluorobenzylideneaniline
m-fluorobenzylideneaniline
p-fluorobenzylideneaniline
N-benzylidene-o-fluoroaniline
N-benzylidene-m-fluoroaniline
N-benzylidene-p-fluoroaniline
N-benzylidene-2,3-difluoroaniline
N-benzylidene-2,4-difluoroaniline
N-benzylidene-2,5-difluoroaniline
N-benzylidene-2,6-difluoroaniline
N-benzylidene-3,4-difluoroaniline
N-benzylidene-3,5-difluoroaniline
N-(o-chlorobenzylidene)-p-trifluoromethylaniline
N-benzylidene-2,3,4-trifluoroaniline
N-benzylidene-2,4,6-trifluoroaniline
N-(o-fluorobenzylidene)-o-fluoroaniline
N-(m-fluorobenzylidene)-o-fluoroaniline
N-(p-fluorobenzylidene)-o-fluoroaniline
N-(o-fluorobenzylidene)-m-fluoroaniline
N-(m-fluorobenzylidene)-m-fluoroaniline
N-(p-fluorobenzylidene)-m-fluoroaniline
N-(o-fluorobenzylidene)-m-fluoroaniline
N-(m-fluorobenzylidene)-m-fluoroaniline
N-(p-fluorobenzylidene)-m-fluoroaniline
N-(2,3-difluorobenzylidene)-o-fluoroaniline
N-(2,4-difluorobenzylidene)-o-fluoroaniline
N-(2,5-difluorobenzylidene)-o-fluoroaniline
N-(2,6-difluorobenzylidene)-o-fluoroaniline
N-(3,4-difluorobenzylidene)-o-fluoroaniline
N-(3,5-difluorobenzylidene)-o-fluoroaniline
N-(2,3,4-trifluorobenzylidene)-o-fluoroaniline
N-(2,4,6-trifluorobenzylidene)-o-fluoroaniline
N-(2,3-difluorobenzylidene)-m-fluoroaniline
N-(2,4-difluorobenzylidene)-m-fluoroaniline
N-(2,5-difluorobenzylidene)-m-fluoroaniline
N-(2,6-difluorobenzylidene)-m-fluoroaniline
N-(3,4-difluorobenzylidene)-m-fluoroaniline
N-(3,5-difluorobenzylidene)-m-fluoroaniline
N-(2,3,4-trifluorobenzylidene)-m-fluoroaniline
N-(2,4,6-trifluorobenzylidene)-m-fluoroaniline
N-(2,3-difluorobenzylidene)-p-fluoroaniline
N-(2,4-difluorobenzylidene)-p-fluoroaniline
N-(2,5-difluorobenzylidene)-p-fluoroaniline
N-(2,6-difluorobenzylidene)-p-fluoroaniline
N-(o-chlorobenzylidene)-p-bromoaniline
N-(2,4-dichlorobenzylidene)-p-bromoaniline
N-benzylidene-2-methyl-3-chloroaniline
N-benzylidene-2-methyl-4-chloroaniline
N-benzylidene-2-methyl-3-fluoroaniline
N-benzylidene-2-methyl-4-fluoroaniline
N-(o-chlorobenzylidene)-2-methyl-3-chloroaniline
N-(o-chlorobenzylidene)-2-methyl-4-chloroaniline
N-(o-chlorobenzylidene)-2-methyl-5-chloroaniline
N-(m-chlorobenzylidene)-2-methyl-3-chloroaniline
N-(m-chlorobenzylidene)-2-methyl-4-chloroaniline
N-(p-chlorobenzylidene)-2-methyl-3-chloroaniline
N-(p-chlorobenzylidene)-2-methyl-4-chloroaniline
N-(p-chlorobenzylidene)-2-methyl-5-chloroaniline N-(m-fluorobenzylidene)-2,4-dichloroaniline
N-(o-fluorobenzylidene)-2,4-dichloroaniline
N-(p-fluorobenzylidene)-2,4-dichloroaniline
N-(o-fluorobenzylidene)-2-methyl-3-chloroaniline
N-(o-chlorobenzylidene)-2-methyl-3-chloroaniline
N-(o-hydroxybenzylidene)-2-methyl-3-chloroaniline
N-(o-methylbenzylidene)-2-methyl-3-chloroaniline
N-(o-ethylbenzylidene)-2-methyl-3-chloroaniline
N-(o-chlorobenzylidene)-2-trifluoromethyl-4-fluoroaniline
N-(o-chlorobenzylidene)-2-trifluoromethyl-4-fluoroaniline
N-(o-chlorobenzylidene)-2-trifluoromethyl-3-fluoroaniline
N-(p-chlorobenzylidene)-2-trifluoromethyl-3-fluoroaniline
N-(p-bromobenzylidene)-2-trifluoromethyl-3-fluoroaniline
N-(p-bromobenzylidene)-2-trifluoromethyl-4-fluoroaniline
N-(p-fluorobenzylidene)-2-trifluoromethyl-4-fluoroaniline
N-(p-phenylbenzylidene)-p-toluidine
N-(p-phenylbenzylidene)-p-bromoaniline
N-(p-phenylbenzylidene)-2-methyl-4-chloroaniline
N-(p-phenylbenzylidene)-2-methyl-4-fluoroaniline
N-(p-phenylbenzylidene)-2-chloro-4-bromoaniline
N-(3-chloro-4-cyclohexylbenzylidene)-4-fluoroaniline
N-(3-chloro-4-cyclohexylbenzylidene)-4-bromoaniline
N-(o-hydroxybenzylidene)-o-chloroaniline
N-(o-hydroxybenzylidene)-m-chloroaniline
N-(o-hydroxybenzylidene)-p-chloroaniline
N-(o-hydroxybenzylidene)-o-fluoroaniline
N-(o-hydroxybenzylidene)-m-fluoroaniline
N-(o-hydroxybenzylidene)-p-fluoroaniline
N-(o-hydroxybenzylidene)-2-methyl-3-chloroaniline
N-(o-hydroxybenzylidene)-2-methyl-4-chloroaniline
N-(o-hydroxybenzylidene)-2,3-dimethylaniline
N-(o-hydroxybenzylidene)-2,4-dimethylaniline
N-(o-hydroxybenzylidene)-o-toluidine
N-(o-hydroxybenzylidene)-m-toluidine
N-(o-hydroxybenzylidene)-p-toluidine
N-(benzylidene)-2,4-dibromoaniline
N-(m-fluorobenzylidene)-2,4-dibromoaniline
N-(m-fluorobenzylidene)-2-methyl-4-iodoaniline
N-(o-fluorobenzylidene)-2,4-dibromoaniline
N-(o-fluorobenzylidene)-2-methyl-4-iodoaniline
N-(m-fluorobenzylidene)-2,4-dibromoaniline
N-(m-fluorobenzylidene)-2-methyl-4-iodoaniline
N-(m-fluorobenzylidene)-3-trifluoromethyl-4-chloroaniline
N-(o-fluorobenzylidene)-3-trifluoromethyl-4-chloroaniline
N-(p-fluorobenzylidene)-3-trifluoromethyl-4-chloroaniline
N-(acyloxybenzylidene)aniline
N-(carboxybenzylidene)-m-toluidine
N-(carbomethoxybenzylidene)-m-toluidine
N-benzylidene-carboxyaniline
N-benzylidene-carbomethoxyaniline
N-benzylidene-methylthioaniline
N-benzylidene-methylsulfonylaniline
N-benzylidene-methylsulfinylaniline
N-benzylidene-acetylthioaniline
N-(carboxylbenzylidene)hydroxyaniline
N-(carboxylbenzylidene)chloroaniline
N-(carboxylbenzylidene)fluoroaniline
N-(methylsulfonylbenzylidene)hydroxyaniline
N-(methylsulfonylbenzylidene)chloroaniline
N-(acetyloxybenzylidene)hydroxyaniline
N-(carbomethoxybenzylidene)chloroaniline
N-(hydroxybenzylidene)carboxyaniline
N-(chlorobenzylidene)carboxyaniline
N-(dihydroxybenzylidene)carboxyaniline
N-(dichlorobenzylidene)carboxyaniline
N-(difluorobenzylidene)carboxyanline
N-(dihydroxybenzylidene)methylsulfonylaniline
N-(dichlorobenzylidene)methylsulfonylaniline
N-(difluorobenzylidene)methylsulfonylaniline
N-(2,3,4-trihydroxybenzylidene)carboxyaniline
N-(3,5-dichlorobenzylidene)-p-carbomethoxyaniline
N-(4-carbomethoxybenzylidene)dichloroaniline
N-(2,4,6-trichlorobenzylidene)carboxyaniline
N-(3,4,5-trifluorobenzylidene)carboxyaniline
N-(p-morpholinobenzylidene)carboxyaniline
N-(p-phenylbenzylidene)carboxyaniline
N-(methylsulfonylbenzylidene)chloroaniline
N-(carboxybenzylidene)chloroaniline
N-(p-carboxybenzylidene)-4-toluidine
N-(p-chlorobenzylidene)-2-[(5-methyl-4-imidazolyl)-methyl mercapto]aniline
N-(2,3-dichlorobenzylidene)carboxyaniline
N-(2,4-dichlorobenzylidene)acetyloxyaniline
N-(2,5-dichlorobenzylidene)methylsulfonylaniline
N-(p-cyanobenzylidene)-3,5-dichloroaniline
N-(p-nitrobenzylidene)-3,5-dichloroaniline
N-(p-carbomethoxybenzylidene)-3,5-dichloroaniline
N-(p-methylsulfonylbenzylidene)-3,5-dichloroaniline
N-(p-chlorobenzyldiene)-2-carboethoxy-4-fluoroaniline
N-(p-carbomethoxybenzylidene)-4-methylaniline
N-(2,3,4-trichlorobenzylidene)-p-carboxyaniline
N-(2,4,6-trichlorobenzylidene)-p-carboxyaniline
N-(o-carboxybenzylidene)-p-trifluoromethylaniline
N-(halo-4-cyclohexylbenzylidene)-4-haloaniline
N-(3-chloro-4-cyclohexylbenzylidene)-4-fluoroaniline
N-(3-chloro-4-cyclohexylbenzylidene)-4-bromoaniline
N-(2,3-difluorobenzylidene)carboxylaniline
N-(2,4-difluorobenzylidene)carboxylaniline
N-(2,5-difluorobenzylidene)carboxylaniline
N-(2,6-difluorobenzylidene)carboxylaniline
N-(3,4-difluorobenzylidene)carboxylaniline
N-(3,5-difluorobenzyldiene)carboxyaniline
N-(2,3,4-trifluorobenzylidene)carboxyaniline
N-(2,4,6-trifluorobenzylidene)methylsulfonylaniline
N-(2,3-difluorobenzylidene)methylsulfonylaniline
N-(2,4-difluorobenzylidene)acetyloxyaniline
N-(2,5-difluorobenzylidene)acetyloxyaniline
N-(2,6-difluorobenzylidene)acetyloxyaniline
N-(2,3,4-trifluorobenzylidene)carboxyaniline
N-(2,4,6-trifluorobenzylidene)carboxyaniline
N-benzylidene-2-methyl-3-carboxyaniline
N-benzylidene-2-methyl-4-carboxyaniline
N-benzylidene-2-methyl-3-acetyloxyaniline
N-benzylidene-2-methyl-4-acetyloxyaniline
N-(chlorobenzylidene)-2-methyl-3-carboxyaniline
N-(chlorobenzylidene)-2-methyl-4-carboxyaniline
N-(chlorobenzylidene)-2-methyl-5-carboxyaniline
N-(chlorobenzylidene)-2-methyl-3-chloroaniline
N-(chlorobenzylidene)-2-methyl-4-acetyloxyaniline
N-(p-carboxybenzylidene)-2-methyl-3-chloroaniline
N-(p-carboxybenzylidene)-2-methyl-4-chloroaniline
N-(p-carboxybenzylidene)-2-methyl-5-chloroaniline
N-(m-carboxybenzylidene)-2,4-dichloroaniline
N-(carboxybenzylidene)-2,4-dichloroaniline
N-(methylsulfonylbenzylidene)-2,4-dichloroaniline
N-(carboxybenzylidene)-2-methyl-3-chloroaniline N-(methylsulfonylbenzylidene)-2-methyl-3-chloroaniline
N-(hydroxybenzylidene)-2-carboxy-3-chloroaniline
N-(methylbenzylidene)-2-carboxy-3-chloroaniline
N-(ethylbenzylidene)-2-methylsulfonyl-3-chloroaniline
N-(p-carboxybenzylidene)-2-trifluoromethyl-4-fluoroaniline
N-(p-carboxybenzylidene)-2-trifluoromethyl-3-fluoroaniline
N-(p-acetyloxybenzylidene)-2-trifluoromethyl-4-fluoroaniline
N-(p-phenylbenzylidene)-2-methyl-4-carboxyaniline
N-(p-phenylbenzylidene)-2-methyl-4-acetyloxyaniline
N-(p-phenylbenzylidene)-2-chloro-4-carboxyaniline
N-(3-chloro-4-cyclohexylbenzylidene)-4-carboxyaniline
N-(o-carboxybenzylidene)-2,3-dimethylaniline
N-(o-carboxybenzylidene)-2,4-dimethylaniline
N-(o-methylsulfonylbenzylidene)-o-toluidine
N-(o-acetyloxybenzylidene)-m-toluidine
N-(o-methylsulfinylbenzylidene)-p-toluidine
N-(fluorobenzylidene)-3-trifluoromethyl-4-carboxyaniline
N-(fluorobenzylidene)-3-trifluoromethyl-4-acetyloxyaniline
N-(fluorobenzylidene)-3-trifluoromethyl-4-methylsulfonylaniline These active materials are applied to the skin in combination with a compatible carrier material which may be aqueous, alcoholic, fatty or a combination of these. Carrier materials as contemplated herein include those materials generally utilized as a base for pharmaceutical preparations such as, for example, creams, milks, ointments, gels, oils, lotions, balms, aerosol sprays or the like. Such carrier materials, in order to be suitable, must be selected on a basis of their dermatological acceptability and compatability with the specific active ingredient of the present invention which is utilized. Preferred among carrier formulations for the active agents of the present invention are creams, milk, ointments, lotions and aerosols.

Examples of suitable carrier materials for the formulation of the compositions of the invention include the paraffins, waxes, vegetable or animal oils and fats such as, for example, olive oil, sesame oil, peanut oil and the like, wool fat, spermaceti, esters of fatty acids such as stearic, palmitic and oleic as well as the acids themselves, glycerides of said acids, ethyl, isopropyl, cetyl, stearyl and palmityl alcohols, emulsifying agents of all common types, e.g., nonionic, anionic or cationic agents suitable for the preparation of both water-in-oil and oil-in-water emulsions, thickeners such as, for example, the commercially available cellulose ethers, trajacanth, alginic acid or salts thereof and the like. A particularly preferred emulsifying agent is polyoxyethylene stearyl ether having a molecular weight of about 700 and commercially available under the trademark Brij J by Atlas Powder Co., Wilmington, Delaware. Additional additives which may be incorporated into the preparations of the invention are preservatives, buffers, pH regulators to adjust the pH thereof to slightly acidic, perfumes, and the like. Other agents which have medicinal or therapeutic value may also be incorporated in the compositions of the invention. Where the preparations of the invention are in the form of aerosol sprays or foams, suitable conventional propellants, i.e. polyhalogenated hydrocarbons are also included therein. It is contemplated that where the compositions of the invention are in aerosol form, the propellent will comprise about 10% by weight of said compositions.

The concentration of the active ingredient in dermatologically acceptable carrier preparations such as contemplated herein is between about 1% and about 30% by weight and preferably between about 2% and about 5% by weight.

Wherein the preparations of the invention contain mixtures of more than one of the active ingredients, such active ingredients may be combined in any proportions. It is preferred, however, to combine two or more of such ingredients in approximately equimolar concentrations.

Compositions in accordance with this invention are useful in the prevention or prophylactic treatment as well as inhibition of epidermal cellular proliferation. Additionally, they are effective in treating accompanying inflammation in those skin conditions which may cause the hyperproliferation. In combination with other known medicaments, the compounds of the present invention are useful in controlling cold sores and relieving the discomforture accompanying this condition. These compositions may be applied freely to the skin. As with any conventional skin treatment preparation, such amounts vary with the particular skin conditions, the sensitivity of the user, the active compound employed and the like. Therefore, the effective amount of the preparations of the invention may be chosen within the discretion of the user or as prescribed by the physician.

The following examples serve further to illustrate the invention, but are not intended to define or to limit the scope of the invention, which is defined in the appended claims.

EXAMPLE 1

A lotion in milk form, having the following composition:

| | | |
|---|---|---|
| Hydrogenated, ethoxylated (10 mol) lanolin | 2.0 | g. |
| Triglyceride of fatty acid of coconut oil | 7.0 | g. |
| Cetylalcohol | 0.6 | g. |
| Stearylalcohol | 0.6 | g. |
| Paraffin oil (light weight) | 5.0 | g. |
| N-(o-chlorobenzylidene)-3-chloro-2-methylaniline | 2.5 | g. |
| Stearic acid | 3.0 | g. |
| Demineralized water | 74.0 | g. |
| Triethanolamine | 0.8 | g. |
| Carboxyvinylpolymer | 2.0 | g. |
| Conservation agent | 2.0 | g. | is manufactured as follows:

A mixture of 2.0 g. hydrogenated, ethoxylated (10 mol) lanolin, 7.0 g. triglyceride of fatty acid of coconut oil, 0.6 g. cetylalcohol, 0.6 g. stearyl alcohol, 5.0 g. paraffin oil, 2.5 g. N-(o-chlorobenzylidene)-3-chloro-2-methylaniline and 3.0 g. of stearic acid are melted at 70° C. After addition of 2.0 g. carboxyvinylpolymer in 74.0 g. demineralized water are added at 70° C. with stirring to the resulting suspension. The mixture is stirred for 15 minutes and then cooled. 0.8 g. of triethanolamine is added at 60° C. The resulting mixture is stirred until cold and a white milk, which is stable at 3,000 rpm for 1 hour, is obtained. The lotion is especially useful in the treatment of psoriasis.

Other lotions identical to that described immediately above are prepared by replacing the N-(o-chlorobenzylidene)-3-chloro-2-methylaniline with any of the active compounds previously mentioned.

EXAMPLE 2

A lotion composed of:

| | | |
|---|---|---|
| Triglyceride of fatty acid of coconut oil | 56.3 | g. |
| Cetylalcohol | 2.6 | g. |
| Stearylalcohol | 10.6 | g. |
| Paraffin oil (light weight) | 8.0 | g. |
| N-benzylidene-p-toluidine | 5.0 | g. |
| Demineralized water | 12.2 | g. |
| Triethanolamine | 0.8 | g. |
| Carboxyvinylpolymer | 2.0 | g. |
| Conservation agent | 2.0 | g. | is manufactured as follows:

A mixture of 56.3 g. triglyceride of fatty acid of coconut oil, 2.6 g. cetylalcohol, 10.6 g. stearyl alcohol, 5.0 g. paraffin oil and 5.0 g. N-benzylidene-p-toluidine are mixed at 70° C. 12.0 g. carboxyvinylpolymer in 12.2 g. demineralized water are added at 70° C. with stirring to the resulting suspension. The mixture is stirred for 15 minutes and then cooled, and 0.8 g. of triethanolamine is added at 60° C. The resulting mixture is stirred until cold and a lotion, which is stable at 3,000 rpm for 1 hour, is obtained.

Other preparations identical to that described immediately above are prepared by replacing the N-benzylidene-p-toluidine with any one of the aforementioned active compounds.

EXAMPLE 3

An ointment is prepared by first mixing 5.0 g. of p-carboxybenzylidene-2-chloroaniline in a hot mixture of 57.5 g. of distilled water, 11.5 g. of propylene glycol and 1 ml. of concentrated ammonia solution. The resulting mixture is heated to 75° C. and added with stirring to a hot (75° C.) mixture of 17.0 g. of glycerine, 4.0 g. of a polyoxyethylene stearyl ether having a molecular weight of about 700. Lactic acid is added while the emulsion is still hot in order to adjust to a pH approximating that of the skin, i.e. about 5.5. After cooling, the resulting cream is further worked utilizing a three-roller frame and filled into tubes.

The product had excellent properties in the relief of inflammation caused by herpes zoster as well as preventing the growth of the rash resulting therefrom by inhibiting the growth of the epidermal cells.

EXAMPLE 4

An ointment is prepared by first mixing 7.0 g. of N-(4-carbomethoxybenzylidene)-3,5-dichloroaniline in a hot mixture of 53.93 g. of distilled water, 14 g. of propylene glycol and 1 ml. of concentrated ammonia solution. The resulting mixture is heated to 75° C. and added with stirring to a hot (75° C.) mixture of 17.0 g. of isopropyl myristate, 4.0 g. of glycerine and 4.0 g. of a polyoxyethylene stearyl ether, molecular weight 700. Lactic acid is then added to the hot emulsion to adjust the pH thereof to approximate the pH of the skin, i.e. about 5.5. After cooling, the resulting cream is further worked using a three-roller frame and filled into tubes.

EXAMPLE 5

An ointment is formed by first mixing 4.0 g. N-(4-nitrobenzylidene)-3,5-dichloroaniline in a hot mixture of 60.3 g. of distilled water, 11.5 g. of propylene glycol and 10.1 g. of sodium hydroxide. The resulting solution is heated to 75° C. and added with stirring to a hot (75° C.) mixture of 15.0 g. isopropyl palmitate, 5.0 g. of glyceryl trioleate and 3.0 g. of polyoxyethylene stearyl ether. Lactic acid is added to the hot emulsion to adjust the pH thereof to about 5.5. After cooling, the resulting cream is further worked using a three-roller frame and filled into tubes.

EXAMPLE 6

An ointment is formed as above by first mixing 7.0 g. N-(4-methylsulfonylbenzylidene)-3,5-dichloroaniline in a hot mixture of 60.83 g. of distilled water, 11.5 g. of propylene glycol and 0.1 g. of sodium hydroxide. The resulting solution is heated to 75° C. and added with stirring to a hot (75° C.) mixture of 13.0 g. polyol diester of capric acid, 5.0 g. of isopropyl myristate and 5.0 g. of polyoxyethylene stearyl ether. Lactic acid is added to the hot emulsion to adjust the pH thereof to about 5.5. After cooling, the resulting cream is further worked using a three-roller frame and filled into tubes. The product has excellent properties when used as an anti-inflammatory agent and to inhibit the growth of cells due to skin conditions of a non-specific origin.

EXAMPLE 7

A composition having the following:

| | | |
|---|---|---|
| Hydrogenated, ethoxylate (10 mol) lanolin | 1.8 | g. |
| Triglyceride of fatty acid of coconut | 7.0 | g. |
| Cetylalcohol | 0.6 | g. |
| Stearylalcohol | 0.6 | g. |
| Paraffin oil (lightweight) | 5.0 | g. |
| N-(p-carboxylbenzylidene)-3-chloro-2-methylaniline | 0.75 | g. |
| Stearic acid | 3.0 | g. |
| Demineralized water | 72.2 | g. |
| Triethanolamine | 0.8 | g. |
| Carboxyvinylpolymer | 2.0 | g. |
| Conservation agent | 2.0 | g. | is manufactured as follows:

A mixture of 1.8 g. hydrogenated, ethoxylated (10 mol) lanolin, 7.0 g. triglyceride of fatty acid of coconut, 0.6 g. cetylalcohol, 0.6 g. stearyl alcohol, 5.0 g. paraffin oil, 0.05 g. hydrocortisone and 3.0 g. of stearic acid are blended at 70° C. After addition of 0.75 g. N-(p-carboxylbenzylidene)-3-chloro-2-methylaniline, 2.0 g. carboxyvinylpolymer in 72.2 g. demineralized water are added at 70° C. with stirring to the resulting suspension. The mixture is stirred for 15 minutes and then cooled. 0.8 g. of triethanolamine is added at 60° C. The resulting mixture is stirred until cold and a white milk, which is stable at 3,000 rpm for one hour, is obtained. Viscosity: 6000 Cp (Brockfield, Spindel, 5, 10 rpm).

EXAMPLE 8

A composition for restricting the area of a psoriasis rash is as follows: 0.5 g of N-(4-chlorobenzylidene)-4-chloro-2-methylaniline and 0.20 g. N-(4-hydroxybenzylidene)-2-methyl-3-chloroaniline are predispersed in 30.0 g. of propylene glycol. The mixture is then homogenized into 97.4 g. of finished cream, ointments or lotion following a modification of any one of the procedures described in F. W. Martin et al, "Remington's Pharmaceutical Sciences", 14th Ed., Mack Publishing Co., Easton, Pa. (1965).

EXAMPLE 9

A lip ointment having the following ingredients:

| | |
|---|---|
| N-(o-chlorobenzylidene)-3-chloro-2-methylaniline | 2.5 g. |
| Camphor | 1.0 g. |
| Phenol | 1.5 g. |
| Mineral Oil | 5.0 g. |
| Beeswax | 3.0 g. |
| Petrolatum | 5.0 g. |
| Paraffin | 2.5 g. |
| Lanolin | 2.0 g. |
| Polyglyceryl-3-diisostearate | 2.0 g. |
| Ethanol | 2.0 g. |
| Sodium Borate | 0.5 g. |
| Ammonium carbonate | 1.0 g. |
| Water | 10.0 g. | is manufactured as follows:

A mixture of 10.0 g. of distilled water, 2.5 g. of N-(o-chlorobenzylidene)-3-chloro-2-methylaniline, 1.0 g. of camphor, 1.5 g. of phenol, 1.0 g. of ammonia and 5.0 g. of mineral oil are heated with stirring to 75° C. To the resulting mixture are added with stirring 3.0 g. beeswax, 2.5 g. of paraffin, 5.0 g. of petrolatum, 2.0 g. of lanolin, 2.0 g. of ethanol, 2.0 g. of polyglyceryl-3-diisostearate, 0.5 g. of sodium borate and 1.0 g. of ammonium carbonate. The mixture is stirred until cold, worked with a three-roller frame and filled into tubes.

The product has excellent properties to prevent and treat cold sores already formed.

We claim:

1. A method of inhibiting or preventing cellular proliferation in mammals which comprises administering to a mammal in need of treatment an effective amount of a compound of the formula:

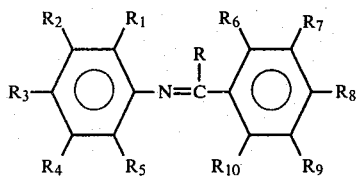 (I)

where:
R is hydrogen or alkyl;
$R_1$, $R_2$, $R_3$, $R_4$, $R_5$, $R_6$, $R_7$, $R_8$, $R_9$, and $R_{10}$ may be the same or different and are
hydrogen,
alkyl,
nitro,
amino,
haloloweralkoxy,
haloloweralkyl,
halo,
loweralkoxy,
hydroxy,
carboxy and
carbalkoxy; and $R_3$ and $R_8$ may also be cycloalkyl, cycloalkenyl or aryl in a suitable pharmaceutically acceptable carrier.

2. The method of claim 1 where the compound applied is N-(o-chlorobenzylidene)-3-chloro-2-methylaniline.

3. The method of claim 1 where the compound applied is N-(2-methyl-3-chlorobenzylidene)-2-hydroxyaniline.

4. The method of claim 1 where the compound applied is o-hydroxybenzylideneaniline.

5. The method of claim 1 where the compound applied is N-(4-chlorobenzylidene)-3,5-dichloroaniline.

6. The method of claim 1 where the compound applied is N-(p-chlorobenzylidene)-2-methyl-3-chloroaniline.

7. The method of claim 1 where the compound applied is N-(m-chlorobenzylidene)-4-fluoroaniline.

8. The method of claim 1 where the compound applied is N-(benzylidene)-3,5-dichloroaniline.

9. The method of claim 1 where the compound applied is N-(p-phenylbenzylidene)-4-bromoaniline.

10. The method of claim 1 where the compound applied is N-(o-chlorobenzylidene)-4-fluoroaniline.

11. The method of claim 1 where the compound applied is N-(benzylidene)-2-methyl-4-fluoroaniline.

12. The method of claim 1 where the compound applied is N-(p-chlorobenzylidene)-m-fluoroaniline.

13. The method of claim 1 where the compound applied is N-(p-chlorobenzylidene)-m-chloroaniline.

14. The method of claim 1 where the compound applied is N-(o-chlorobenzylidene)-2-methyl-4-chloroaniline.

15. The method of claim 1 where the compound applied is N-(p-phenylbenzylidene)-2-chloro-4-bromoaniline.

16. The method of claim 1 where the compound applied is N-(p-chlorobenzylidene)-2-methyl-3-chloroaniline.

17. The method of claim 1 where the compound applied is N-(p-chlorobenzylidene)-2-methyl-4-chloroaniline.

18. The method of claim 1 where the compound applied is N-(3-chloro-4-cyclohexylbenzylidene)-4-fluoroaniline.

19. The method of claim 1 where the compound applied is N-(3-chloro-4-cyclohexylbenzylidene)-4-bromoaniline.

20. The method of claim 1 where the compound applied is N-(p-phenylbenzylidene)-p-methylaniline.

21. The method of claim 1 where the compound applied is N-(p-phenylbenzylidene)aniline.

22. The method of claim 1 where the compound applied is N-(2,6-dichlorobenzylidene)-p-chloroaniline.

23. The method of claim 1 where the compound applied is N-benzylidene-o-toluidine.

24. The method of claim 1 where the compound applied is N-(4-chlorobenzylidene)-4-fluoro-2-trifluoromethylaniline.

25. The method of claim 1 where the compound applied is N-(p-bromobenzylidene)-4-fluoro-2-trifluoromethylaniline.

26. The method of claim 1 where the compound applied is N-(p-fluorobenzylidene)-2-trifluoromethylaniline.

27. The method of claim 1 where the compound applied is N-(o-chlorobenzylidene)-3-chloroaniline.

* * * * *